United States Patent
Ashton et al.

(10) Patent No.: US 9,445,906 B2
(45) Date of Patent: Sep. 20, 2016

(54) MEDICAL DEVICE AND METHOD

(75) Inventors: Roger Ashton, Warwick (GB); Rachel Miller, Shropshire (GB)

(73) Assignee: Smith & Nephew, Inc., Memphis, TN (US)

( * ) Notice: Subject to any disclaimer, the term of this patent is extended or adjusted under 35 U.S.C. 154(b) by 569 days.

(21) Appl. No.: 13/148,015

(22) PCT Filed: Feb. 4, 2010

(86) PCT No.: PCT/GB2010/000199
§ 371 (c)(1),
(2), (4) Date: Oct. 12, 2011

(87) PCT Pub. No.: WO2010/089555
PCT Pub. Date: Aug. 12, 2010

(65) Prior Publication Data
US 2012/0029651 A1 Feb. 2, 2012

(30) Foreign Application Priority Data

Feb. 4, 2009 (GB) .................................. 0901795.5

(51) Int. Cl.
  *A61F 2/34* (2006.01)
  *A61F 2/36* (2006.01)
  *A61F 2/30* (2006.01)

(52) U.S. Cl.
  CPC .............. *A61F 2/3609* (2013.01); *A61F 2/34* (2013.01); *A61F 2002/30116* (2013.01); *A61F 2002/30245* (2013.01); *A61F 2002/30253* (2013.01); *A61F 2002/30654* (2013.01); *A61F 2002/30657* (2013.01); *A61F 2002/30658* (2013.01); *A61F 2002/30934* (2013.01); *A61F 2002/30937* (2013.01); *A61F 2002/3482* (2013.01); *A61F 2002/3496* (2013.01); *A61F 2002/3498* (2013.01); *A61F 2002/3623* (2013.01); *A61F 2230/0076* (2013.01)

(58) Field of Classification Search
  CPC ............. A61F 2002/30657–2002/3066; A61F 2002/3441; A61F 2002/3482; A61F 2002/3496–2002/3498; A61F 2002/30159
  See application file for complete search history.

(56) References Cited

U.S. PATENT DOCUMENTS

| | | | | |
|---|---|---|---|---|
| 4,784,662 A | * | 11/1988 | Muller | 623/22.21 |
| 4,919,675 A | * | 4/1990 | Dietschi | A61F 2/34 |
| | | | | 623/22.26 |
| 5,928,285 A | * | 7/1999 | Bigliani et al. | 623/19.13 |

(Continued)

OTHER PUBLICATIONS

Chinese Office Action; State Intellectual Property Office of People's Republic of China; Chinese Patent Application No. 201080015272.9; Dec. 22, 2014; 6 pages.

*Primary Examiner* — Yashita Sharma
*Assistant Examiner* — Rebecca Preston
(74) *Attorney, Agent, or Firm* — Taft Stettinius & Hollister LLP

(57) ABSTRACT

A receptacle for receiving a mating member in an orthopedic joint, wherein the receptacle comprises: a first portion shaped so as to contact with the mating member, in normal use; a second portion shaped so as to not contact with the mating member, in normal use, wherein the first portion comprises a non-spherical surface. A mating member for being received by a receptacle, wherein the mating member comprises: a first portion shaped so as to contact with the receptacle, in normal use; a second portion shaped so as to not contact with the receptacle, in normal use, wherein the first portion comprises a non-spherical surface. Also disclosed are receptacles and heads of generally elliptical shape.

20 Claims, 14 Drawing Sheets

(56) References Cited

U.S. PATENT DOCUMENTS

| | | | |
|---|---|---|---|
| 6,059,830 A * | 5/2000 | Lippincott et al. | 623/18.11 |
| 2004/0143341 A1 * | 7/2004 | McLean | 623/22.15 |
| 2005/0060039 A1 * | 3/2005 | Cyprien | 623/19.13 |
| 2008/0188944 A1 * | 8/2008 | Ernsberger | 623/22.15 |
| 2009/0171466 A1 * | 7/2009 | Frazee et al. | 623/23.43 |

* cited by examiner

Compression Axis

Compression Axis

MEDICAL DEVICE AND METHOD

This application is a United States National Phase filing of International Application No. PCT/2010/000199 filed on Feb. 4, 2010 which claims priority from UK provisional application No. 0901795.5 entitled "Medical Device and Method" filed on Feb. 4, 2009, both of which are herein incorporated in their entirety.

The present invention relates to receptacles and corresponding mating members. In particular, the present invention relates to orthopaedic joint prostheses designed to replace diseased or failed ball and socket joints.

Under normal circumstances, the ball and socket elements are considered to be rigid elements, whose geometry is defined during design and manufacture. In reality both elements can undergo deformation on installation into the body, either through the mechanical forces imposed on them during use, or through forces temporarily imposed on them during the installation process. The deformations on these components can be either permanent or transient, depending on the nature of the prosthesis materials used, or on the size of forces experienced by the components of the prosthesis. There is described herein a novel approach to the consideration and mitigation of the effects of these deformations.

Conventionally, the mating parts of the ball and socket joint are considered to be partial spheres. For ball and socket joints that are principally designed to maximise fluid film lubrication, these spheres are generally of high geometric accuracy and high surface finish and their relative sizes are such that there is a small difference between them, usually referred to as the clearance. This clearance allows for the ingress of any lubricating fluids that may be present, thereby reducing the rotational friction in the ball and socket joint when the joint is in motion.

This optimal clearance is small and is less than 0.5% of the diameter of the ball and socket bearing. If this clearance is reduced substantially, then the lubricant ingress may be impeded thus elevating the rotational friction of the bearing. This has the consequence of imposing excessive frictional torque on to the bone attachments of the device, giving rise to early failure through inhibition of bone in-growth and loosening of the attachments of the device. If the clearance becomes too large, then the function of the lubricant is impaired by virtue of the lessening of the contact area between the ball and the socket and adverse changes to the lubricant entrainment geometry around the contact area of the bearing.

Considering the cup component, this usually consists of a hemispherical outer surface which makes contact with the prepared acetabulum of the body, and an inner/interior region (perhaps) partial sphere which comprises the cup bearing surface. On a press fit device, the acetabulum is usually prepared with a corresponding spherical surface by means of spherical reaming tools. The spherical prepared surface has a smaller diameter than that of the outer surface of the cup, hence when it is forcibly placed in position, the cup device experiences compressive forces from the prepared surface of the acetabulum which act on it in a way to change its shape. These forces may be uniform around the open diameter of the cup, or non-uniform depending on the nature of the acetabulum. Hence the forces act on the cup device so as to reduce its effective size through deformation, but also may act in a non-uniform manner so as to render the bearing surface of the device no longer sufficiently spherical to support the appropriate lubrication properties.

Further forces that result from weight bearing will act on the cup component. These will also serve to either reduce the overall diameter of the cup bearing surface, or render the device sufficiently non-spherical so as to impair the bearing properties.

The size of these deformations are generally in the region of 0.5% of the bearing diameter and can hence influence the performance of the bearing by changing the frictional torque transmitted by the bearing in operation.

The head component may also undergo some shape changes due to installation. Where the head component is of thin section and requires any degree of press fit on the prepared bone of the femur, as is the case with both cemented and un-cemented resurfacing femoral components, then any errors in the preparation of the femur away from designed specification will lead to asymmetric internal loading of the head component. This is turn will give rise to deviations of the originally round component. This in turn will give rise to aberrations in the spherical surface of the head, so contributing to the impairment of the bearing properties.

The present invention aims to overcome the above problems.

Embodiments of the present invention provide the surgeon with cup and head devices that have corresponding allowances for the deformations that are experienced. Accordingly, an advantage of embodiments of the present invention is that they reduce the net effect of all these deformations occurring during installation and operation.

According to a first aspect of the present invention, there is provided a receptacle for receiving a mating member, wherein the receptacle comprises:
  a first portion shaped so as to contact with the mating member, in use;
  a second portion shaped so as to not contact with the mating member, in use,
  wherein the first portion comprises a non-spherical surface.

The first portion may further comprise a spherical surface.

According to a second aspect of the present invention, there is provided a receptacle for receiving a mating member, wherein the receptacle comprises:
  a first portion shaped so as to contact with the mating member, in use;
  a second portion shaped so as to not contact with the mating member, in use,
  wherein the first portion comprises an asymmetric surface.

The feature of the first portion comprising an asymmetric surface means that the surface does not have rotational symmetry about an axis intersecting the receptacle.

The first portion may further comprise a symmetric surface.

The feature of the first portion comprising a symmetric surface means that the surface has rotational symmetry about an axis intersecting the receptacle.

According to a third aspect of the present invention, there is provided a receptacle for receiving a mating member, wherein the receptacle comprises:
  a first portion shaped so as to contact with the mating member, in use;
  a second portion shaped so as to not contact with the mating member, in use,
  wherein the surfaces of the first portion and the second portion are discontinuous.

According to a fourth aspect of the present invention, there is provided a receptacle for receiving a mating member, wherein the receptacle comprises:

a first portion shaped so as to contact with the mating member, in use;

a second portion shaped so as to not contact with the mating member, in use, wherein at least one of the first portion and the second portion is shaped so as to compensate for any deformation of the receptacle, in use.

According to a fifth aspect of the present invention, there is provided a mating member for being received by a receptacle, wherein the mating member comprises:

a first portion shaped so as to contact with the receptacle, in use;

a second portion shaped so as to not contact with the receptacle, in use, wherein the first portion comprises a non-spherical surface.

The first portion may further comprise a spherical surface.

According to a sixth aspect of the present invention, there is provided a mating member for being received by a receptacle, wherein the mating member comprises:

a first portion shaped so as to contact with the receptacle, in use;

a second portion shaped so as to not contact with the receptacle, in use, wherein the first portion comprises an asymmetric surface.

The first portion may further comprise a symmetric surface.

According to a seventh aspect of the present invention, there is provided a mating member for being received by a receptacle, wherein the mating member comprises:

a first portion shaped so as to contact with the receptacle, in use;

a second portion shaped so as to not contact with the receptacle, in use, wherein the surfaces of the first portion and the second portion are discontinuous.

According to an eighth aspect of the present invention, there is provided a mating member for being received by a receptacle, wherein the mating member comprises:

a first portion shaped so as to contact with the receptacle, in use;

a second portion shaped so as to not contact with the receptacle, in use, wherein at least one of the first portion and the second portion is shaped so as to compensate for any deformation of the mating member and/or receptacle, in use.

In the first to the eighth aspects of the present invention, the second portion is shaped so as to not contact with the mating member in normal use. During extremes of motion, it is possible that the second portion may momentarily contact with the mating member.

The term deformation may mean deflection or distortion of the receptacle.

The term compensate may mean to avoid deformation of the receptacle.

The term compensate may mean to prevent deformation of the receptacle.

The term compensate may mean to mitigate deformation of the receptacle.

The term compensate may mean to minimise deformation of the receptacle.

According to a ninth aspect of the present invention, there is provided a system comprising a receptacle according to any of the first to fourth aspects in combination with a mating member according to any of the fifth to eighth aspects.

Devices and systems according to the first to ninth aspects of the present invention enable direct contact of the bearing surfaces. That is, there may be no clearance between the bearing surfaces. Such devices are made of materials exhibiting very low friction.

According to a tenth aspect of the present invention, there is provided a receptacle for receiving a mating member, wherein the receptacle comprises:

a first portion shaped so as to mate with the mating member, in use;

a second portion shaped so as to not mate with the mating member, in use, wherein the first portion comprises a non-spherical surface shaped such that fluid may flow between the receptacle and the mating member, in use.

The first portion may further comprise a spherical surface.

According to an eleventh aspect of the present invention, there is provided a receptacle for receiving a mating member, wherein the receptacle comprises:

a first portion shaped so as to mate with the mating member, in use;

a second portion shaped so as to not mate with the mating member, in use, wherein the first portion has an asymmetric surface shaped such that fluid may flow between the receptacle and the mating member.

The feature of the first portion comprising an asymmetric surface means that the surface does not have rotational symmetry about an axis intersecting the receptacle.

The first portion may further comprise a symmetric surface.

The feature of the first portion comprising a symmetric surface means that the surface has rotational symmetry about an axis intersecting the receptacle.

According to a twelfth aspect of the present invention, there is provided a receptacle for receiving a mating member, wherein the receptacle comprises:

a first portion shaped so as to mate with the mating member, in use;

a second portion shaped so as to not mate with the mating member, in use, wherein the first portion and the second portion are discontinuous, and wherein the first portion is shaped such that fluid may flow between the receptacle and the mating member.

According to a thirteenth aspect of the present invention, there is provided a receptacle for receiving a mating member, wherein the receptacle comprises:

a first portion shaped so as to mate with the mating member, in use;

a second portion shaped so as to not mate with the mating member, in use, wherein the first portion is shaped so as to compensate for deformation of the receptacle, and wherein the first portion is shaped such that fluid may flow between the receptacle and the mating member.

The term deformation may mean deflection or distortion of the receptacle.

The term compensate may mean to avoid deformation of the receptacle.

The term compensate may mean to prevent deformation of the receptacle.

The term compensate may mean to mitigate deformation of the receptacle.

The term compensate may mean to minimise deformation of the receptacle.

According to a fourteenth aspect of the present invention, there is provided a mating member for being received by a receptacle, wherein the mating member comprises:
- a first portion shaped so as to mate with the receptacle, in use;
- a second portion shaped so as to not mate with the receptacle, in use,
- wherein the first portion comprises a non-spherical surface shaped such that fluid may flow between the receptacle and the mating member.

The first portion may further comprise a spherical surface.

According to a fifteenth aspect of the present invention, there is provided a mating member for being received by a receptacle, wherein the mating member comprises:
- a first portion shaped so as to mate with the receptacle, in use;
- a second portion shaped so as to not mate with the receptacle, in use,
- wherein the first portion has an asymmetric surface shaped such that fluid may flow between the receptacle and the mating member.

The first portion may further comprise a symmetric surface.

According to a sixteenth aspect of the present invention, there is provided a mating member for being received by a receptacle, wherein the mating member comprises:
- a first portion shaped so as to mate with the receptacle, in use;
- a second portion shaped so as to not mate with the receptacle, in use,
- wherein the first portion and the second portion are discontinuous, and wherein the first portion is shaped such that fluid may flow between the receptacle and the mating member.

According to a seventeenth aspect of the present invention, there is provided a mating member for being received by a receptacle, wherein the mating member comprises:
- a first portion shaped so as to mate with the receptacle, in use;
- a second portion shaped so as to not mate with the receptacle, in use,
- wherein at least one of the first portion and the second portion is shaped so as to compensate for any deformation of the mating member and/or receptacle, in use, and wherein the first portion is shaped such that fluid may flow between the receptacle and the mating member.

In the tenth to the seventeenth aspects of the present invention, the second portion is shaped so as to not contact with the mating member in normal use. During extremes of motion, it is possible that the second portion may momentarily contact with the mating member.

The term deformation may mean deflection or distortion of the receptacle.

The term compensate may mean to avoid deformation of the receptacle.

The term compensate may mean to prevent deformation of the receptacle.

The term compensate may mean to mitigate deformation of the receptacle.

The term compensate may mean to minimise deformation of the receptacle.

According to an eighteenth aspect of the present invention, there is provided a system comprising a receptacle according to any of the tenth to thirteenth aspects of the present invention in combination with a mating member according to any of the fourteenth to seventeenth aspects of the present invention.

Devices and systems according to the tenth to eighteenth aspects of the present invention enable fluid to ingress and/or flow into the gap formed between the receptacle and the mating member during use (e.g. during articulation of a hip prosthesis). The fluid may be a lubricant. The fluid may be synthetic. The fluid may be natural. The fluid may be bodily fluid. The fluid may be synovial fluid.

According to a nineteenth aspect of the present invention, there is provided a receptacle for receiving a mating member, wherein the receptacle comprises a mating surface defined by a scalene or prolate ellipsoid.

According to a twentieth aspect of the present invention, there is provided a receptacle in the form of a cup having a superior, first part and an inferior, second part, wherein the first and second portions have different radial values.

The radial value of the first part relative to the second part may be given by the ratio R1/R2, wherein R1/R2 is in the range 0.995310 to 0.999999.

R1/R2 may be in the range 0.996603 to 0.999199.

The centres of R1 and R2 may be separated by a distance X1 in a direction along the face of the cup such that X1 is in the range 178 to 416.

X1 may be in the range 208 to 312.

The centres of R1 and R2 may be separated by a distance Z1 in a direction along the axis of the cup such that Z1 is in the range 156 to 312.

Z1 may be in the range 178 to 250.

A receptacle or mating member according to any aspect of the present invention, wherein the receptacle is a socket.

A receptacle or mating member according to any aspect of the present invention, wherein the receptacle is a cup.

A receptacle or mating member according to any aspect of the present invention, wherein the receptacle is a hemisphere.

A receptacle or mating member according to any aspect of the present invention, wherein the receptacle is a partial hemisphere.

A receptacle or mating member according to any aspect of the present invention, wherein the receptacle is an insert.

A receptacle or mating member according to any aspect of the present invention, wherein the first portion is a bearing surface.

A receptacle or mating member according to any aspect of the present invention, wherein the mating surface is a bearing surface.

A receptacle or mating member according to any aspect of the present invention, wherein the mating member is a moveable member.

A receptacle or mating member according to any aspect of the present invention, wherein the mating member is a ball.

A receptacle or mating member according to any aspect of the present invention, wherein the mating member is a head.

A receptacle or mating member according to any aspect of the present invention, wherein at least one of the receptacle or the mating member is made at least in part of a material selected from the group consisting of metal, metal alloy, ceramic, plastics and combinations thereof.

According to a twenty-first aspect of the present invention, there is provided a system comprising a receptacle according to any relevant aspect of the present invention in combination with a mating member according to any relevant aspect of the present invention.

According to a twenty-second aspect of the present invention, there is provided a cup for receiving a head, wherein the cup comprises a mating surface defined by the equation:

$$\frac{x^i}{a^l} + \frac{y^j}{b^m} + \frac{z^k}{c^n} = 1$$

wherein:
x is defined as a direction corresponding to that of maximum cup deflection;
y is in a direction parallel to the face of the cup and perpendicular to x;
z is a perpendicular to both x and y;
a is radius along x axis;
b is radius along y axis;
c is radius along z axis;
a>b and a>c; and
i, j, k, l, m, n are 1 or more.

According to some embodiments of the present invention, at least one of i, j, k, l, m or n may be an integer.

According to some embodiments of the present invention, at least one of i, j, k, l, m or n may be a non-integer.

According to a twenty-third aspect of the present invention, there is provided a cup for receiving a head, wherein the cup comprises a mating surface defined by the equation:

$$\frac{x^i}{a^l} + \frac{y^j}{b^m} + \frac{z^k}{c^n} = 1$$

wherein:
x is defined as a direction corresponding to that of maximum cup deflection;
y is in a direction parallel to the face of the cup and perpendicular to x;
z is a perpendicular to both x and y;
a is radius along x axis;
b is radius along y axis;
c is radius along z axis;
a>b and a>c;
b/a is in the range 0.9900 to 0.9998;
c/a is in the range 0.9900 to 0.9998;
b/c is in the range 1.0100 to 0.9900; and
i, j, k, l, m, n are 1 or more.

According to some embodiments of the present invention, at least one of i, j, k, l, m or n may be an integer.

According to some embodiments of the present invention, at least one of i, j, k, l, m or n may be a non-integer.

According to a twenty-fourth aspect of the present invention, there is provided a cup for receiving a head, wherein the cup comprises a mating surface defined by the equation:

$$\frac{x^2}{a^2} + \frac{y^2}{b^2} + \frac{z^2}{c^2} = 1,$$

wherein:
x is defined as a direction corresponding to that of maximum cup deflection;
y is in a direction parallel to the face of the cup and perpendicular to x;
z is a perpendicular to both x and y;
a is radius along x axis;
b is radius along y axis;
c is radius along z axis;
a>b and a>c;
b/a is in the range 0.9900 to 0.9998;
c/a is in the range 0.9900 to 0.9998; and
b/c is in the range 1.0100 to 0.9900.

According to some embodiments of the present invention, b/a may be in the range 0.997601918 to 0.9998, c/a may be in the range 0.996522782 to 0.998919568 and b/c may be in the range 0.999879822 to 1.002286127.

The direction corresponding to that of the maximum cup deflection may be in the direction parallel to the face of the cup and passing through both the illium and ischium. The direction may be generally along a line between the anterior inferior illiac spine and the ischial tuberosity.

According to a twenty-fifth aspect of the present invention, there is provided a head for mating with a cup, wherein the head comprises a mating surface defined by the equation:

$$\frac{x^i}{a^l} + \frac{y^j}{b^m} + \frac{z^k}{c^n} = 1$$

wherein:
z is defined to lie on or close to the axis of the neck to which the head is attached and in a direction towards the cup in normal use;
x is defined to be perpendicular to z and lying along a plane through z which also passes through the point of contact between the head and the cup;
y is defined to be perpendicular to both x and z;
a is radius along x axis;
b is radius along y axis;
c is radius along z axis;
a>b and a>c; and
i, j, k, l, m, n are 1 or more.

According to some embodiments of the present invention, at least one of i, j, k, l, m or n may be an integer.

According to some embodiments of the present invention, at least one of i, j, k, l, m or n may be a non-integer.

According to a twenty-sixth aspect of the present invention, there is provided a head for mating with a cup, wherein the head comprises a mating surface defined by the equation:

$$\frac{x^i}{a^l} + \frac{y^j}{b^m} + \frac{z^k}{c^n} = 1$$

wherein:
z is defined to lie on or close to the axis of the neck to which the head is attached and in a direction towards the cup in normal use;
x is defined to be perpendicular to z and lying along a plane through z which also passes through the point of contact between the head and the cup;
y is defined to be perpendicular to both x and z;
a is radius along x axis;
b is radius along y axis;
c is radius along z axis;
a<b and a<c;
b/a is in the range 1.0100 to 1.0002;
c/a is in the range 1.0100 to 1.0002;
b/c is in the range 1.010 to 0.9900; and
i, j, k, l, m, n are 1 or more.

According to some embodiments of the present invention, at least one of i, j, k, l, m or n may be an integer.

According to some embodiments of the present invention, at least one of i, j, k, l, m or n may be a non-integer.

According to a twenty-seventh aspect of the present invention, there is provided a head for mating with a cup, wherein the head comprises a mating surface defined by the equation:

$$\frac{x^2}{a^2}+\frac{y^2}{b^2}+\frac{z^2}{c^2}=1,$$

wherein:
- z is defined to lie on or close to the axis of the neck to which the head is attached and in a direction towards the cup in normal use;
- x is defined to be perpendicular to z and lying along a plane through z which also passes through the point of contact between the head and the cup;
- y is defined to be perpendicular to both x and z;
- a is radius along x axis;
- b is radius along y axis;
- c is radius along z axis;
- a<b and a<c;
- b/a is in the range 1.0100 to 1.0002;
- c/a is in the range 1.0100 to 1.0002; and
- b/c is in the range 1.010 to 0.9900.

According to a twenty-eighth aspect of the present invention, there is provided a system comprising a cup according to any of the twenty-second to twenty-fourth aspects of the present invention in combination with a head according to any of the twenty-fifth to twenty-seventh aspects of the present invention.

Reference will now be made, by way of example, to the accompanying figures, in which:

FIG. 1b is an alternative representation of the cup device shown in FIG. 1a;

FIG. 2b is an alternative representation of the cup device shown in FIG. 2a;

According to some embodiments of the present invention, the cup device has a working bearing area in the region of the cup where most contact is likely to occur. This is in the superior aspect of the cup (see "first part" in FIGS. 1a, 1b, 2a and 2b). The working bearing area/first part of the embodiment shown in FIGS. 2a and 2b is larger than the working bearing area/first part of the embodiment shown in FIGS. 1a and 1b. The working bearing area has a particular diametric value. The working bearing area has a largely circular or elliptical boundary, or some such shape as is deemed to represent the normal working area of the cup.

The area surrounding this working area (see "second part" in FIGS. 1a, 1b, 2a and 2b) is carefully removed in such a manner so as to prevent the surrounding area from coming into contact with the head component, even when the cup component has been asymmetrically deformed by the physiological loading. To achieve this, the surrounding area is removed in a shape, whereby the largest amount of material is removed in the inferior aspect of the cup and the amount of material removed in this relieved area, decreases to a minimum in the superior aspect of the cup (see the cross-sections depicted in FIGS. 3 to 5). Hence the cup component can be considered to be asymmetric about its centreline, where its centreline is defined as the line through the centre of the working sphere of the bearing that is perpendicular to the face of the cup. This removed area may be spherical in itself, and may be differing in diameter but not lying on the same centreline as the working bearing area. The distance between the cup centreline and the centreline of the larger removed area may be in the region of 0.05 mm to 0.15 mm. Furthermore, the centres of two spherical regions may not lie on the same plane with respect to the plane perpendicular to the axis of the cup component. The separation of the two centres should be in the region of 0.05 mm to 0.15 mm.

Figure 3:
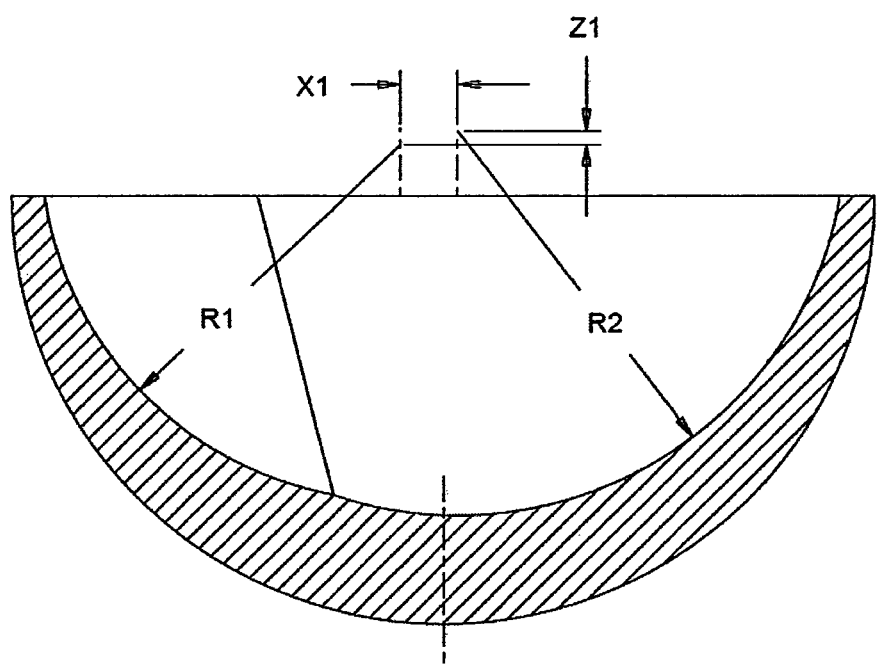
FIG. 3 shows a cross-section of the cup device shown in FIGS. 1a and 1b.

FIG. 3 shows the dimensioned cross section of a cup whose internal shape consists of two intersecting partial spheres, whose radii are R1 and R2, respectively, and whose centres are separated by X1 in the x direction and Z1 in the z direction.

For clarity, in FIG. 3, the values of X1 and Z1 are exaggerated so that the separation of the centres of R1 and R2 can be seen. In addition, for clarity, the values of R1, R2, X1 and X2 are set so as to indicate that the first partial sphere of radius R1 can be considerably smaller than the area of the partial sphere whose radius is R2. Indeed, the relative areas of the two spheres are in no way constrained by the construction shown and could be equal, smaller or greater than each other.

Figure 4:
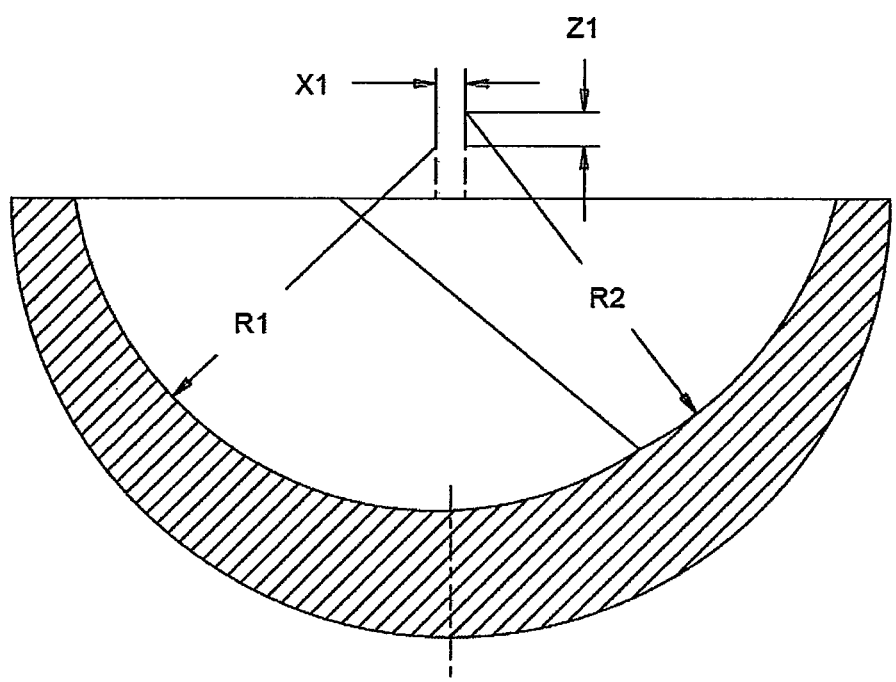
FIG. 4 shows a cross-section of the cup device shown in FIGS. 2a and 2b.

FIG. 4 is the exact same construction as FIG. 3, but the values of R1, R2, X1 and Z1 have been adjusted so as to support this point, in that the area of the partial sphere of radius R1 is considerably larger than the area of the partial sphere of radius R2.

Figure 5:
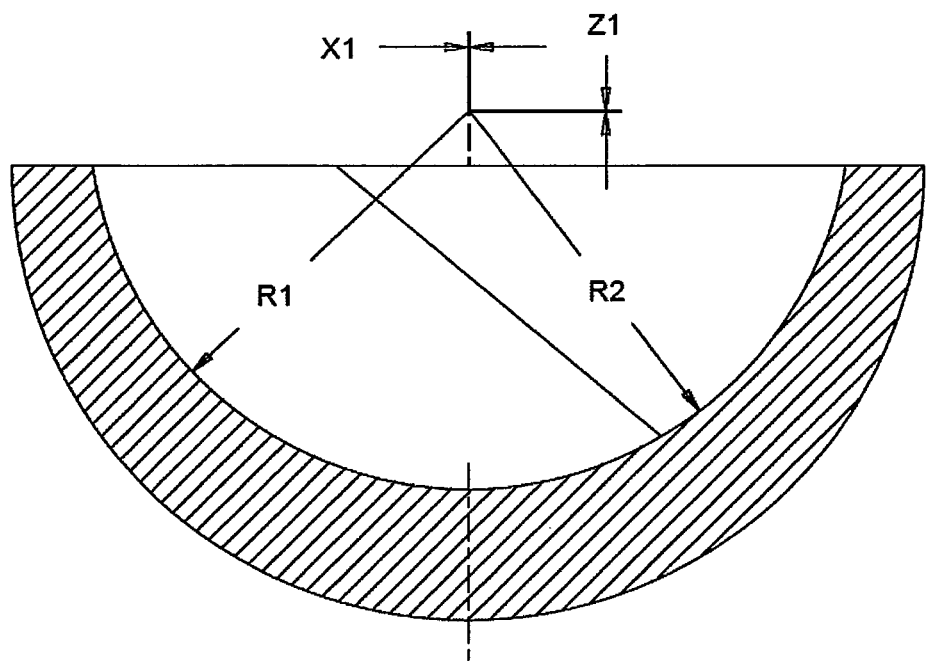
FIG. 5 shows a cross-section of the cup device shown in FIGS. 2a and 2b.

FIG. 5 is of the exact same construction as FIGS. 3 and 4, but with the relative values of R1, R2, X1 and Z1 being such that the centres of the two partial spheres appear to lie on the same centreline as the outer surface of the cup. This is simply due to the value of X1 being smaller in value than the thickness of the drawn line.

Figure 6:
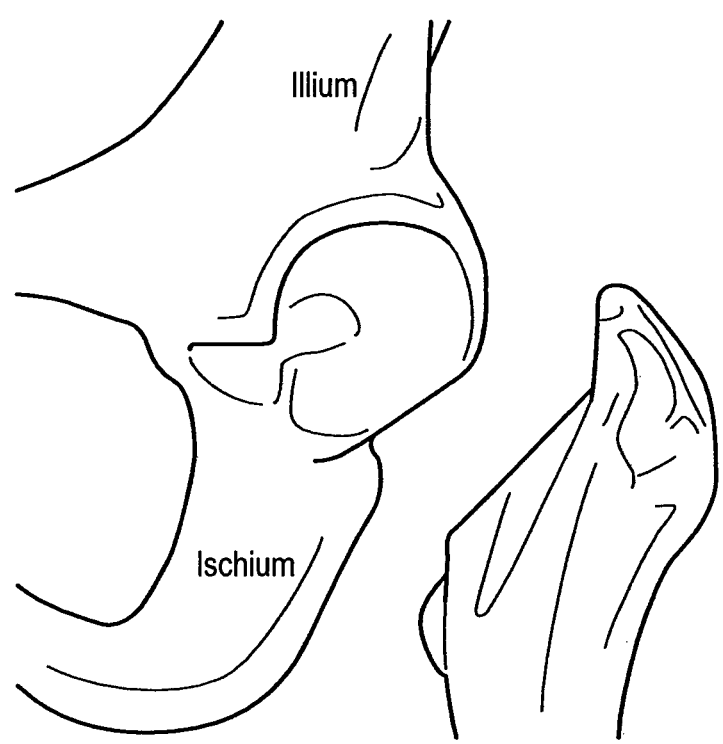
FIG. 6 shows an acetabulum.

FIG. 6 shows an acetabulum, indicating the illium and the ischium anatomical features.

Figure 1A:
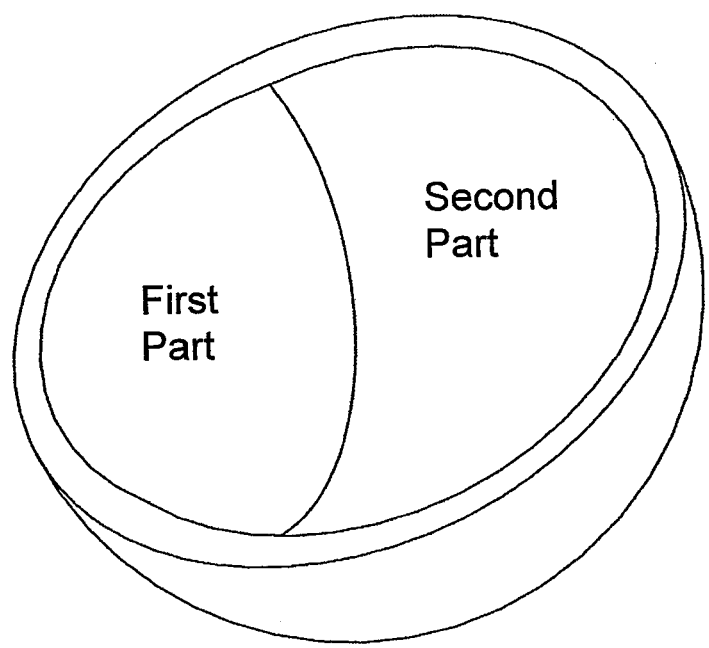
FIG. 1a shows a cup device according to an embodiment of the present invention.
Figure 1B:
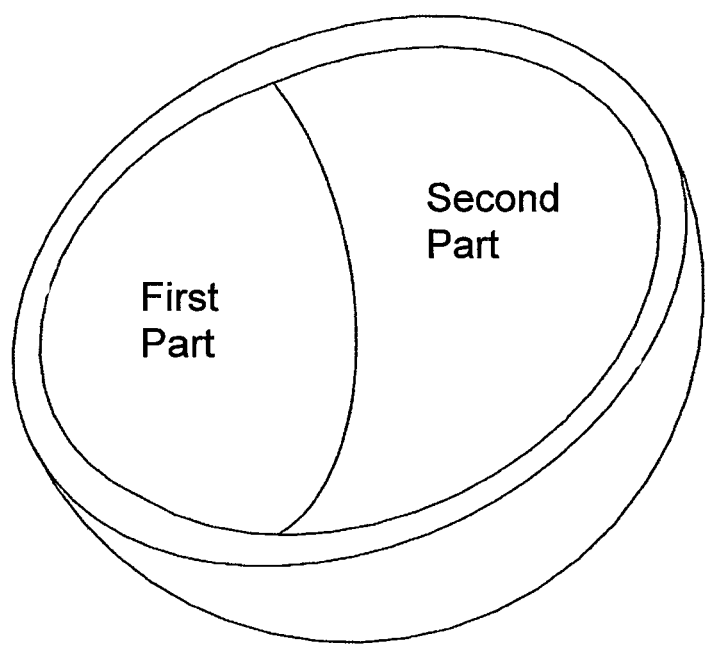
Figure 2A:
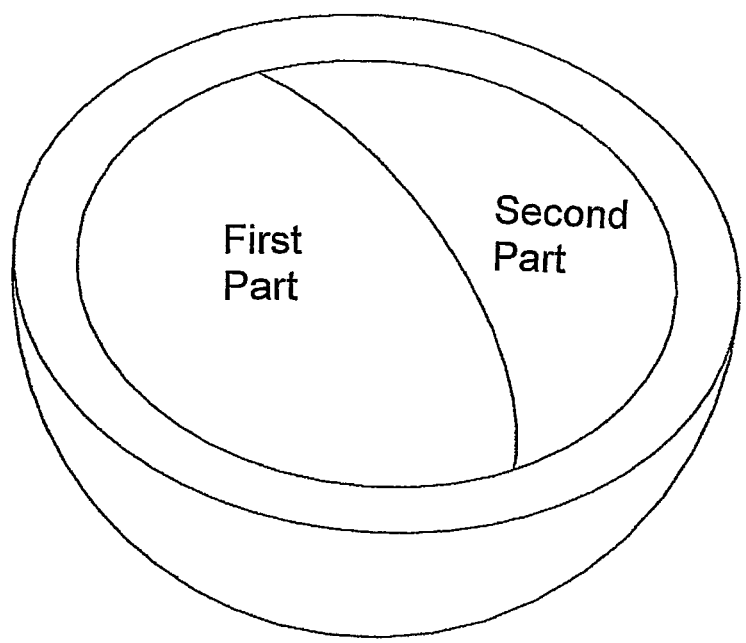
FIG. 2a shows a cup device according to an embodiment of the present invention.
Figure 2B:
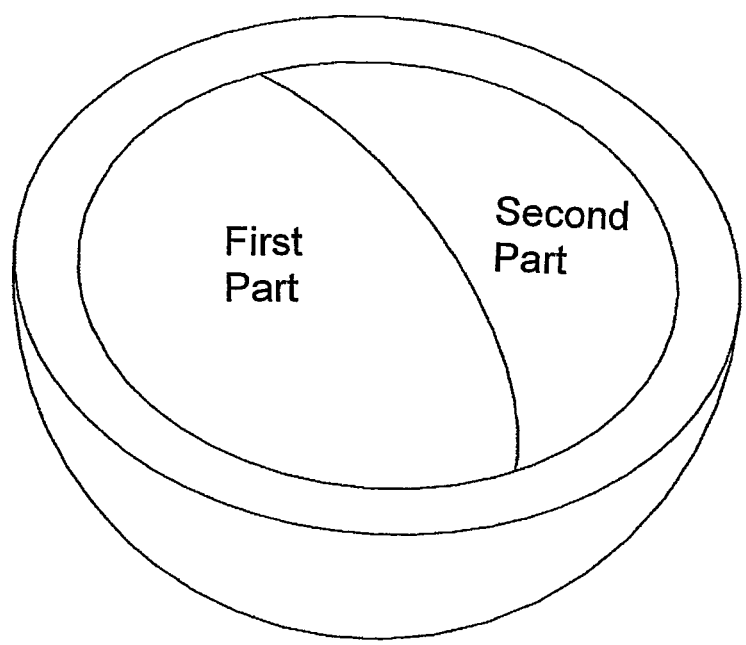
Figure 7:
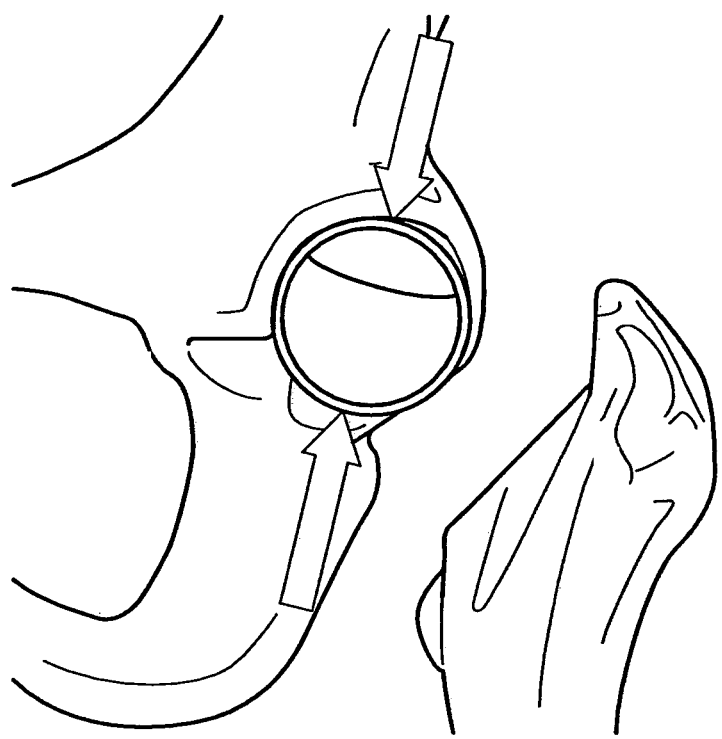
FIG. 7 shows the cup device of FIGS. 1a and 1b implanted in an acetabulum.

FIG. 7 shows the cup device of FIGS. 1a and 1b implanted in an acetabulum and indicates a compression axis passing through the illium and ischium.

Figure 8:
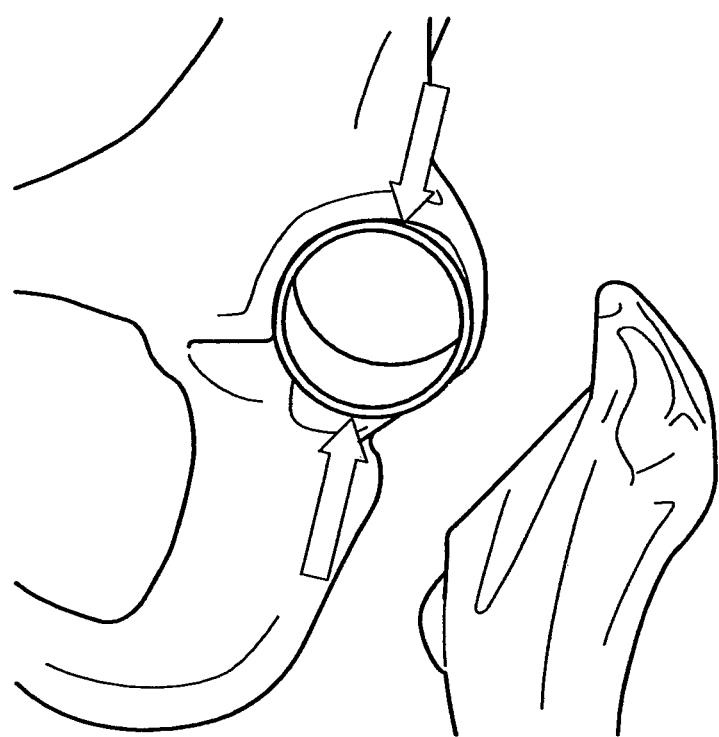
FIG. 8 shows the cup device of FIGS. 2a and 2b implanted in an acetabulum.

FIG. 8 shows the cup device of FIGS. 2a and 2b implanted in an acetabulum and indicates a compression axis passing through the illium and ischium.

Figure 9:
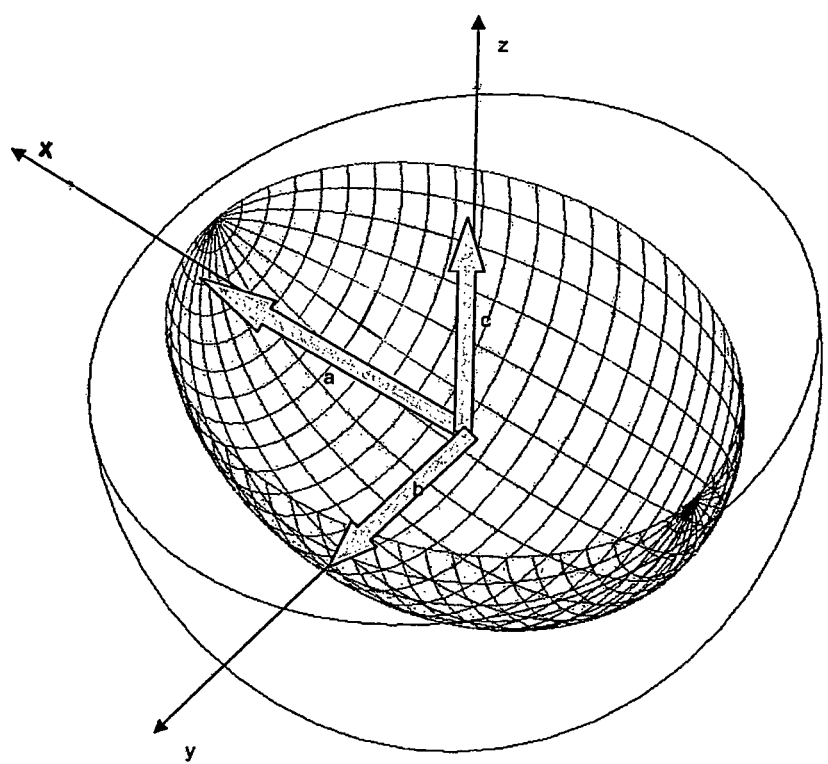
FIG. 9 shows a schematic of a cup device according to an embodiment of the present invention.

According to some embodiments of the present invention, the entire inner bearing surface may be considered to be defined as a scalene or prolate ellipsoid whose geometry may be described by the following equation:

$$\frac{x^2}{a^2}+\frac{y^2}{b^2}+\frac{z^2}{c^2}=1$$

where, according to FIG. 9:
- x is defined as a direction corresponding to that of maximum cup deflection, typically in the direction parallel to the face of the cup and passing through both ileum and ischium;
- y is in a direction parallel to the face of the cup and perpendicular to x;
- z is a perpendicular to both x and y;
- a=radius along x axis, b=radius along y axis and c=radius along z axis;
- a>b and a>c;
- b/a is in the range 0.9900 to 0.9998;
- c/a is in the range 0.9900 to 0.9998; and
- b/c is in the range 1.0100 to 0.9900.

Figure 10:
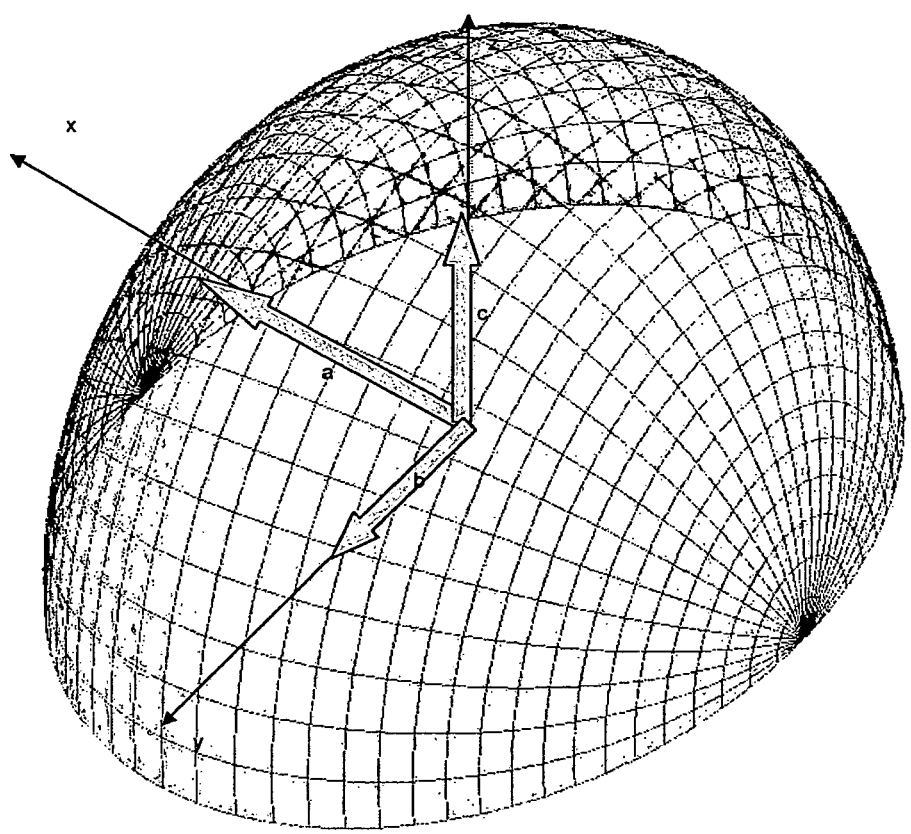
FIG. 10 shows a schematic of a head device according to an embodiment of the present invention.

According to some embodiments of the present invention, the material is removed from the head component in such a manner that the required compensation in the clearance that mitigates the cup deflection is provided by the ellipsoid shape of the head. In this case, the geometry may be described by the above equation, but according to FIG. 10:
- a<b and a<c;
- b/a is in the range 1.0100 to 1.0002;
- c/a is in the range 1.0100 to 1.0002; and
- b/c is in the range 1.010 to 0.9900.

Figure 11:
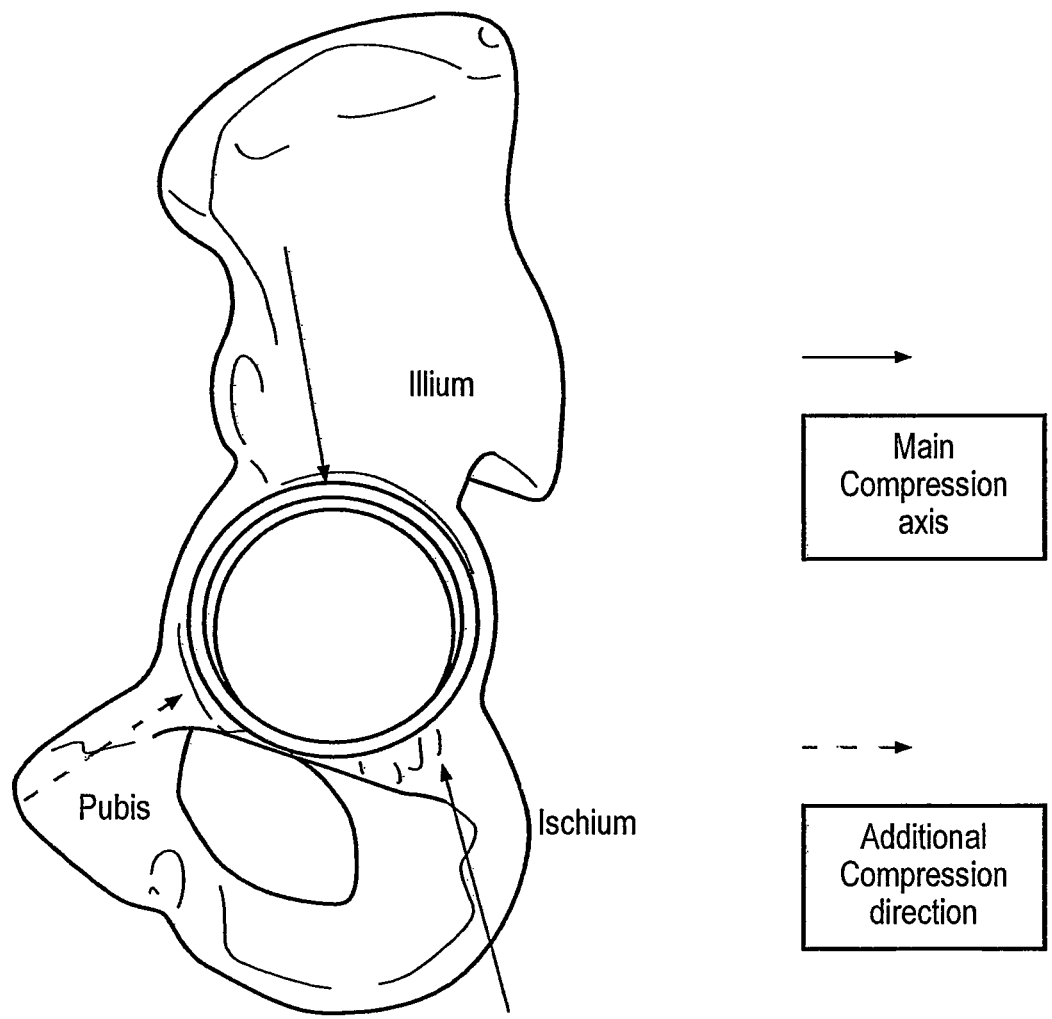
FIG. 11 shows a cup device according to an embodiment of the present invention implanted in an acetabulum.
Figure 12:
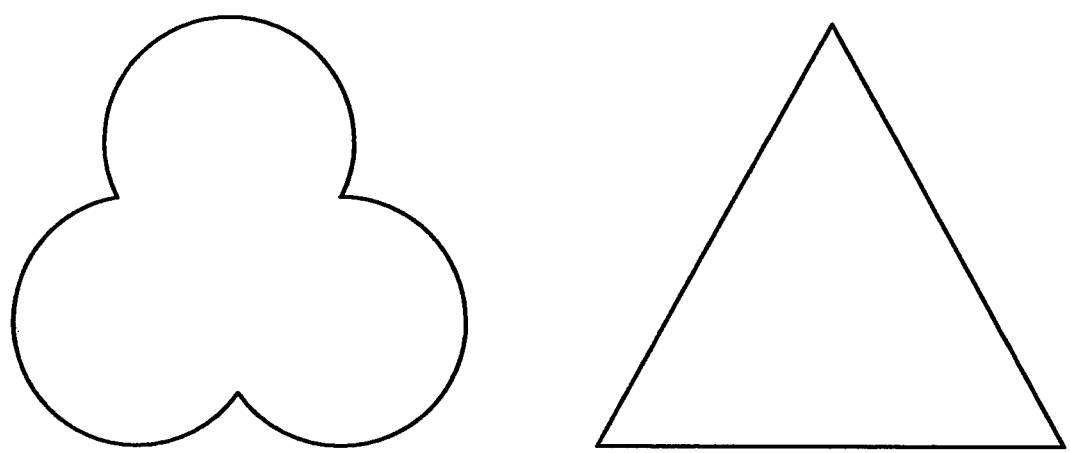
FIG. 12 is a schematic of two types of deformation shape corresponding to the implanted device shown in FIG. 11.

FIG. 11 shows a cup device according to an embodiment of the present invention implanted in an acetabulum. In addition to the main compression axis passing through the illium and ischium, a further compression axis is shown passing through the pubis. FIG. 12 is a schematic of two possible types of deformation shape corresponding to the implanted device shown in FIG. 11, resulting from the two compression axes indicated in FIG. 11.

The invention claimed is:

1. A receptacle in the form of a cup for receiving a mating member, the receptacle comprising:
   an interior first portion having a superior, first part defining a first radial value; and
   an interior second portion having an inferior, second part defining a second radial value,
   wherein the first and second radial values are different;
   wherein the first radial value of the first part has a first radial center, wherein the second radial value of the second part has a second radial center, and wherein the first and second radial centers are separated from one another; and
   wherein the first portion is a bearing surface, and wherein the second portion is a substantially non-bearing surface;
   wherein the cup defines an interior region surrounded by a lip, the interior region defining an inner mating surface sized and shaped for receipt of the mating member, said inner mating surface including the interior first and second portions defining the first and second radial values, wherein the inner mating surface is asymmetrical relative to a centerline of the receptacle;
   wherein the superior first part and the inferior second part intersect one another, and wherein each of the superior first part and the inferior second part extend to the lip of the cup; and
   wherein the first radial value R1 of the first part relative to the second radial value R2 of the second part is given by the ratio R1/R2, and wherein R1/R2 is in the range 0.995310 to 0.999999.

2. A receptacle according to claim 1, wherein R1/R2 is in the range 0.996603 to 0.999199.

3. A receptacle in the form of a cup for receiving a mating member, the receptacle comprising:
   an interior first portion having a superior, first part defining a first radial value; and
   an interior second portion having an inferior, second part defining a second radial value,
   wherein the first and second radial values are different;
   wherein the first radial value of the first part has a first radial center, wherein the second radial value of the second part has a second radial center, and wherein the first and second radial centers are separated from one another; and
   wherein the first portion is a bearing surface, and wherein the second portion is a substantially non-bearing surface;
   wherein the cup has a partial hemispherical shape and defines an interior region surrounded by a lip, the interior region defining an inner mating surface sized and shaped for receipt of the mating member, said inner mating surface including the interior first and second portions defining the first and second radial values, wherein the inner mating surface is asymmetrical relative to a centerline of the receptacle; and
   wherein the superior first part and the inferior second part intersect one another, and wherein each of the superior first part and the inferior second part extend to the lip of the cup, and wherein the first radial value R1 of the first part relative to the second radial value R2 of the second part is given by the ratio R1/R2, and wherein R1/R2 is in the range 0.995310 to 0.999999.

4. A receptacle according to claim 3, wherein the receptacle is an insert.

5. A receptacle according to claim 3, wherein the superior, first part defining the first radial value extends over a first area;
   wherein the inferior, second part defining the second radial value extends over a second area; and
   wherein the first area is smaller than the second area.

6. A receptacle according to claim 3, wherein the superior, first part defining the first radial value extends over a first area;
   wherein the inferior, second part defining the second radial value extends over a second area; and
   wherein the first area is larger than the second area.

7. A receptacle according to claim 3, wherein the superior, first part defines a first partial spherical surface; and
   wherein the inferior, second part defines a second partial spherical surface; and
   wherein the first and second partial spherical surfaces intersect one another.

8. A receptacle according to claim 3, wherein the first and second radial centers are separated from one another in a direction along a face of the receptacle.

9. A receptacle according to claim 3, wherein the first and second radial centers are separated from one another in a first direction extending along a diameter of the receptacle.

10. A receptacle according to claim 9, wherein the first and second radial centers are separated from one another in a second direction substantially perpendicular to the first direction.

11. A receptacle according to claim 3, wherein the first and second radial centers are separated from one another along two dimensions.

12. A receptacle according to claim 3, wherein the superior first part and the inferior second part define the entire interior region of the cup surrounded by the lip.

13. A receptacle according to claim 3, wherein the interior region of the cup defines a partial hemispherical-shaped surface surrounded by the lip, the partial hemispherical-shaped surface entirely defined by the superior first part and the inferior second part.

14. A receptacle according to claim 3, wherein the superior first part and the inferior second part define an intersection extending across the interior region of the cup from a first point on the lip to a second point on the lip.

15. A receptacle in the form of a cup for receiving a mating member, the receptacle comprising:
   an interior first portion having a superior, first part defining a first radial value; and
   an interior second portion having an inferior, second part defining a second radial value, wherein the first and second radial values are different;
   wherein the first radial value of the first part has a first radial center, wherein the second radial value of the second part has a second radial center, and wherein the first and second radial centers are separated from one another;
   wherein the first portion is shaped so as to contact the mating member, in normal use; and
   wherein the second portion is shaped so as to not contact the mating member, in normal use;
   wherein the cup defines an interior region surrounded by a lip, the interior region defining an inner mating surface sized and shaped for receipt of the mating member, said inner mating surface including the interior first and second portions defining the first and second radial values, wherein the inner mating surface is asymmetrical relative to a centerline of the receptacle; and
   wherein the superior first part and the inferior second part intersect one another, and wherein each of the superior first part and the inferior second part extend to the lip of the cup, and
   wherein the interior region of the cup defines a partial hemispherical-shaped surface surrounded by the lip, the partial hemispherical-shaped surface entirely defined by the superior first part and the inferior second part, and wherein the first radial value R1 of the first part relative to the second radial value R2 of the second part is given by the ratio R1/R2, and wherein R1/R2 is in the range 0.995310 to 0.999999.

16. A receptacle according to claim 15, wherein the first and second radial centers are separated from one another in a first direction extending along a diameter of the receptacle.

17. A receptacle according to claim 16, wherein the first and second radial centers are separated from one another in a second direction substantially perpendicular to the first direction.

18. A receptacle according to claim 15, wherein the first and second radial centers are separated from one another along two dimensions.

19. A receptacle according to claim 15, wherein the superior first part and the inferior second part define the entire interior region of the cup surrounded by the lip.

20. A receptacle according to claim 15, wherein the superior first part and the inferior second part define an intersection extending across the interior region of the cup from a first point on the lip to a second point on the lip.

* * * * *